United States Patent [19]
Gijsbers et al.

[11] Patent Number: 5,843,148
[45] Date of Patent: Dec. 1, 1998

[54] HIGH RESOLUTION BRAIN STIMULATION LEAD AND METHOD OF USE

[75] Inventors: Johannes T. M. Gijsbers, Mustergeleen; Frank L. H. Gielen, Eckelrade; Henricus M. Knuth, Kerkrade, all of Netherlands

[73] Assignee: Medtronic, Inc., Minneapolis, Minn.

[21] Appl. No.: 721,816

[22] Filed: Sep. 27, 1996

[51] Int. Cl.$^6$ .............................. A61B 5/04; A61N 1/05
[52] U.S. Cl. .................. 607/116; 600/378; 600/373; 600/544
[58] Field of Search ..................... 607/115–139; 606/32; 128/639, 642; 600/373–375, 377, 378, 382, 544

[56] References Cited

U.S. PATENT DOCUMENTS

| | | |
|---|---|---|
| 164,184 | 6/1875 | Kidder . |
| 932,775 | 6/1909 | Gaston . |
| 3,804,098 | 4/1974 | Friedman . |

OTHER PUBLICATIONS

3387 DBS Lead for Brain Stimulation Lead Implant Manual.
3388 Lead Implant Manual.

Primary Examiner—Lee S. Cohen
Assistant Examiner—David M. Ruddy
Attorney, Agent, or Firm—Michael J. Jaro; Harold Patton

[57] ABSTRACT

A brain stimulation lead for precise delivery of electrical stimuli to a small dense brain target, and method of positioning such lead optimally in the patient's brain, is provided. The lead has a distal end portion which is substantially tubular or cylindrical along a longitudinal axis, and has a plurality of electrodes characterized by a diagonal geometry, permitting a greater number of electrodes to be provided within a very small lineal distance, e.g. 10 mm or even 5 mm. In a preferred embodiment, three ring electrodes are positioned on the distal end portion, each at a common angle of about 45 degrees and each extending only about 180° around the lead body. The ring segment electrodes are about 0.5 mm in axial length, and have a separation of about 0.5 mm. The lead also has a tip electrode with a substantially spherical distal edge, and a proximal diagonal edge having the same angle as the ring segment electrodes. The diagonal ring geometry permits fine adjustment of the electrode assembly with respect to the target by simply rotating the lead about its axis, thereby facilitating an optimal electrode placement for precise stimulation of the target.

19 Claims, 4 Drawing Sheets

HIGH RESOLUTION BRAIN STIMULATION LEAD AND METHOD OF USE

FIELD OF THE INVENTION

This invention relates to brain stimulation leads and methods of employing such leads and, more particularly, a brain stimulation lead characterized by having a high resolution tip and method of placing such a lead.

BACKGROUND OF THE INVENTION

Brain stimulation leads designed to electrically stimulate nerve structures in specific areas of the brain are coming into increasing use. Deep brain stimulation has been used in the management of chronic intractable pain of neuropathic and or nociceptive origin. In addition, brain stimulation is very important for treatment of movement disorders. Implantation of a brain stimulation lead into a patient's brain, and delivery of stimulus pulses from a pulse generator to the lead electrodes, produces nerve impulses which may result in inhibition of pain. However, there is now a demand for such stimulation leads which are better able to stimulate exclusively certain selected small neurological targets, and without damage to involved brain tissue, which demand can not be met by existing leads. An example of such a small neurological brain target, for which extremely precise stimulation is needed, is the SubThalamic Nucleus (STN); another application is Globus Pallidus internal (Gpi) stimulation. Other like high density brain targets also require more precise stimulation than is presently available.

The problem that is addressed requires a stimulation lead with high spatial resolution electrodes. The highest resolution lead presently available, such as the Model 3387 RESDBS™, made by Medtronic, Inc., has plural electrodes, each with a length of 1.5 mm, and an electrode separation of 0.5 mm. For such a lead, only one of the four electrodes can be positioned in a small target such as the STN. However, the functional spatial resolution in this target, combined with possible slight movements in the brain, require that more than one active electrode must be made available inside the target. Specifically, the need is to provide up to 4 electrodes within a 10 mm spacing, which imposes extreme requirements on lead construction. Additionally, it is desired to provide a brain stimulation lead, and method of using same, with a highly rigid, tip-bottomed stylet, to permit use of a stereotactic approach of the brain target, preferably without need for a guiding cannula.

SUMMARY OF THE INVENTION

It is a primary object of this invention to provide a brain stimulation lead, and method of placing such lead, which presents an improved high spatial resolution tip carrying a plurality of electrodes that can be used in stimulating small neurological brain targets. In accordance with this object, the invention comprises a stimulation lead for delivery of electrical stimuli to a patient's brain which has a distal end portion carrying a plurality of diagonally spaced ring segment electrodes. The distal end is substantially cylindrical along a longitudinal axis, and each of the plurality of electrodes is diagonally positioned at a common angle relative to the lead axis. Each ring electrode is diagonally around the lead axis and is separated from the adjacent electrodes by about 0.5 mm, depending on the target. In addition, the lead carries a distal tip electrode which is spherically configured at its distal end, and diagonally configured at its proximal end with the common angle to the axis. In a preferred embodiment, the lead distal portion carries three ring electrodes and a tip electrode, the four electrodes being positioned within a distance of no more than about 10 mm. The ring electrodes may extend about 180° around the lead axis, or may extend for a smaller or a greater angle. In another embodiment, a greater number of ring segment electrodes are used, each electrode being less than 90 degrees around the lead, and the optimum plurality of electrodes is selected after testing different combinations of the ring segment electrodes at time of implant, or whenever an adjustment is desired.

In the method of this invention, the lead with high spatial resolution tip is positioned in the patient's brain with a stereotactic instrument, and adjusted axially, i.e., in an in-line direction. After this, finer tuning of the electrode positions for optimum stimulation is achieved simply by rotating the lead, thus re-arranging the relative positions of the ring segment electrodes within the target area.

DESCRIPTION OF THE PREFERRED EMBODIMENTS

Figure 1A:
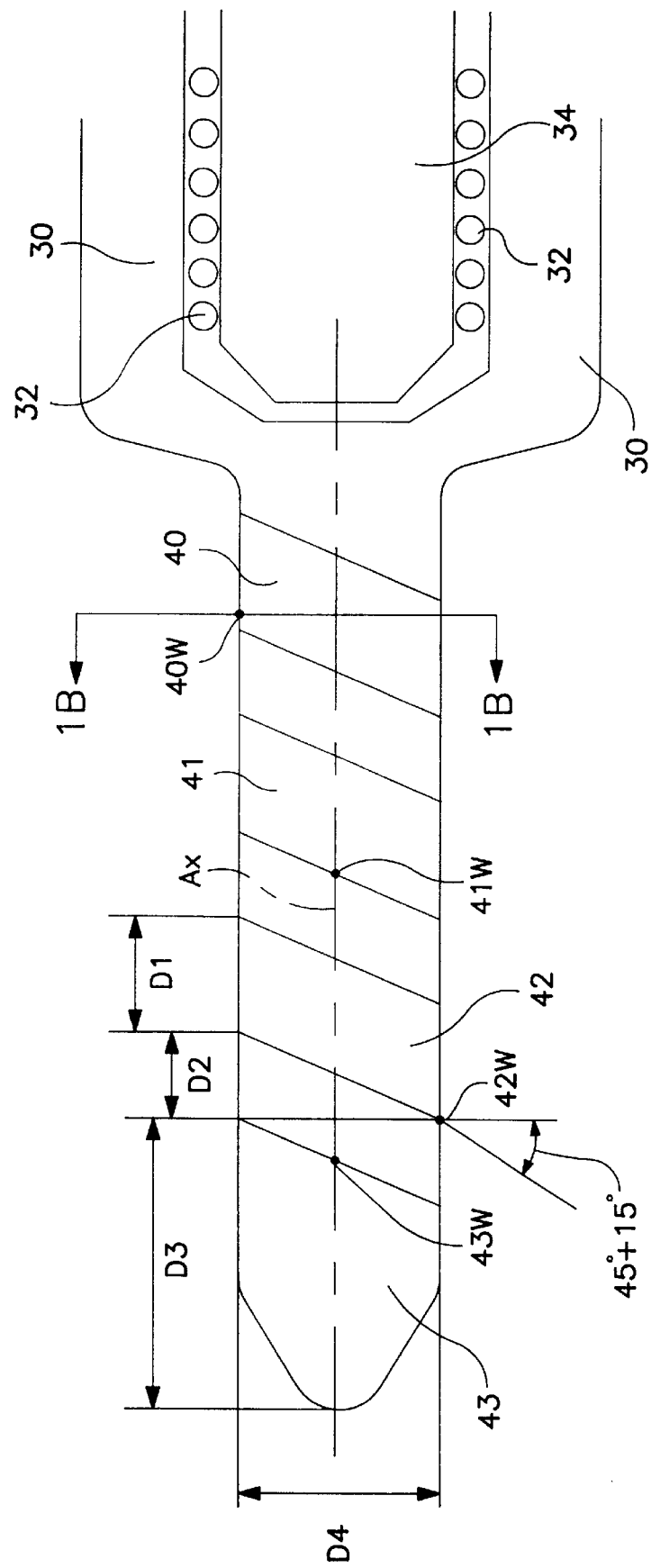
FIG. 1A is a diagrammatic drawing of the distal end of the brain stimulation lead of this invention, showing the relation of the electrodes to each other and to the main lead body, and illustrating the diagonal ring geometry.
Figure 1B:
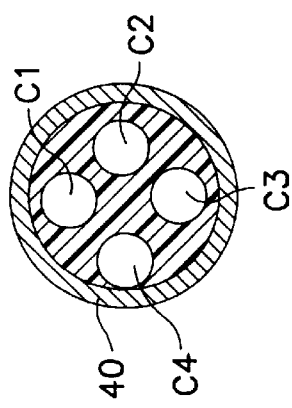
FIG. 1B is a cross section of the lead of FIG. 1A, taken along line A—A of FIG. 1.

Referring now to FIGS. 1A and 1B, there is illustrated the preferred embodiment of the brain stimulation lead of this invention. The lead body 30 is tubular, or cylindrical in form, and has a proximal end (not shown) with suitable connectors for connecting to a pulse stimulator. Lead body 30 suitably has a coating of a biocompatible material such as polyurethane, with a diameter typically of about 0.13 cm. Contained within the lead body is a multi-conductor coil 32, each conductor being individually insulated, connecting the pulse generator to respective electrodes carried by the distal end portion of the lead. The lead has a lumen, within coil 32, in which is placed a stylet shown as 34 at the time of implant. The use of a highly rigid stylet provides the possibility of performing stereotactic placement without the need of any addition aid such as a cannula. The use of a stereotactic instrument, and of a stylet, is well known in the art. See, for example, U.S. Pat. No. 5,464,446, incorporated herein by reference.

Figure 3B:
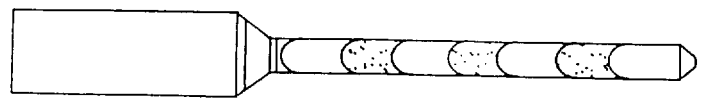
FIGS. 3A and 3B illustrate lead having diagonal ring electrodes characterized by a different surface geometry.
Figure 3A:
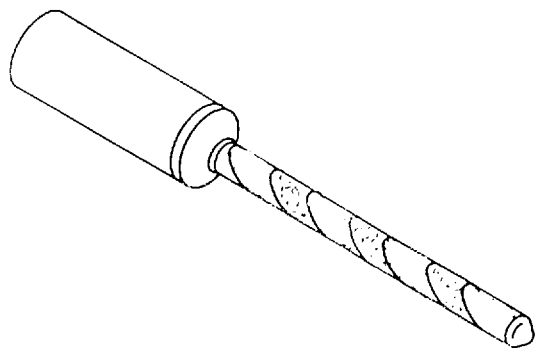

Still referring to FIGS. 1A and 1B, the design of the distal portion, which carries the ring segment electrodes, can be seen. In this exemplary embodiment, three ring segment electrodes are shown, at 40, 41 and 42. As seen in FIG. 1B, each ring electrode illustrated as being about 180°; for this embodiment, each ring is a segment which preferably extends within a range of 180°±45°. As used in describing this invention, the term "ring" is not limited in terms of the angle that it extends around the lead axis, nor in terms of the exact geometry. See the illustration of FIGS. 3a and 3b, discussed hereinbelow. Each diagonal ring electrode is suitably made of platinum iridium and embedded into the biocompatible coating, and has an axial length D1 of about 0.4 to 0.5 mm, although it could be as great as 0.8 mm. The spacing D2 between each ring segment electrode is suitably about 0.5 mm, although it could be within a range of 0.5 to 1.5 mm, depending greatly on the application. The diagonal angle, as indicated, is ideally 45 degrees relative to the lead axis $A_x$, but can be plus/minus 15 degrees. The tip electrode 43 has a roughly spherical distal surface, an axial length of about 0.8 to 1.6 mm, and a distal boundary which is diagonal at the common angle of the ring electrodes, e.g., 45 degrees. The outer diameter D4 of the distal portion, which is positioned in the patient's brain, is preferably 0.5 mm, but can be in the range of 0.3 to 1.2 mm, depending on the application.

As seen in FIG. 1B, for this embodiment, the ring segment is shown as extending about 180° around the cylindrical distal body, although this angle can be adapted within a range of about 135 to 225 degrees. Each electrode is connected to a respective conductor C1, C2, C3 or C4 by a laser weld, as illustrated at 40W, 41W, 42W and 43W.

Figure 2:
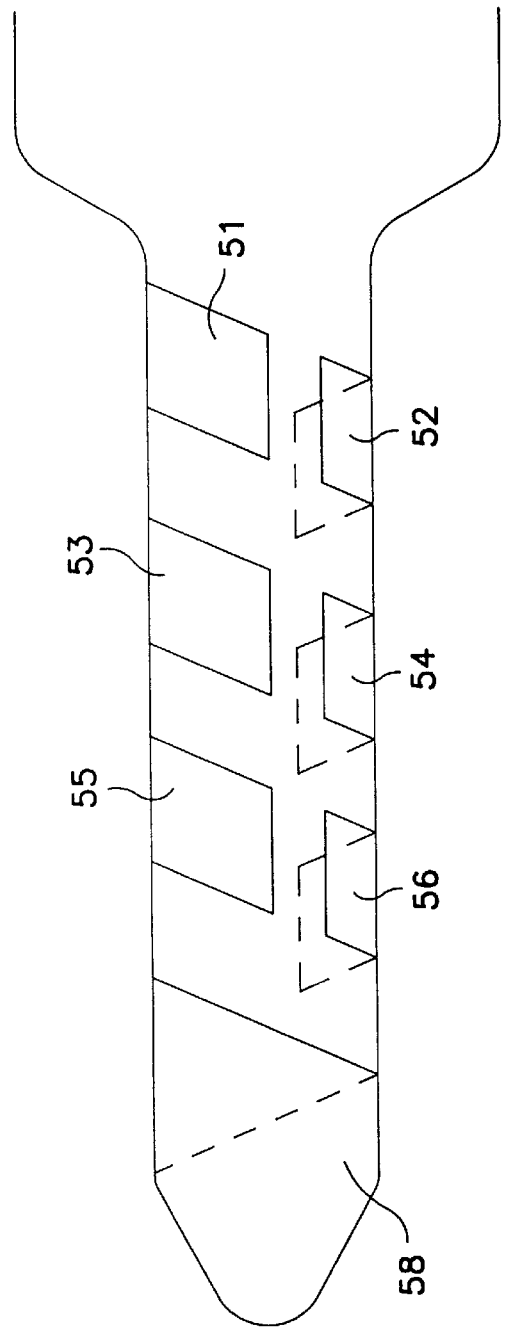
FIG. 2 is a diagrammatic drawing of another embodiment of the brain stimulation lead of this invention, illustrating a distal portion having more than three ring segment diagonally spaced electrodes, the electrodes being positioned to provide a variety of electrode combination choices.

Referring now to FIG. 2, there is shown an alternate embodiment characterized by more than three diagonal ring segment electrodes, each being less than 90 degrees in arc, and each being connected to a respective separate conductor, thereby providing a greater menu of effective electrode choices while maintaining the required high spatial resolution. In this example, there are six ring segment electrodes, designated 51–56, and a tip electrode 58, each of which has a common diagonal geometry to permit positioning of the electrodes on the same size distal portion. In use of this lead, any two or more electrodes can be electrically connected together at the pulse generator site, to provide an optimal electrode configuration Referring now to FIGS. 3A and 3B, there is shown another illustration of a lead distal tip in accordance with this invention. In this embodiment, the electrodes 71, 72, 73, 74 are diagonally oriented, but have a curved surface geometry which contrasts with that of conventional ring electrodes. This illustrates that the invention is not limited in the exact form of the ring electrodes.

Figure 4:
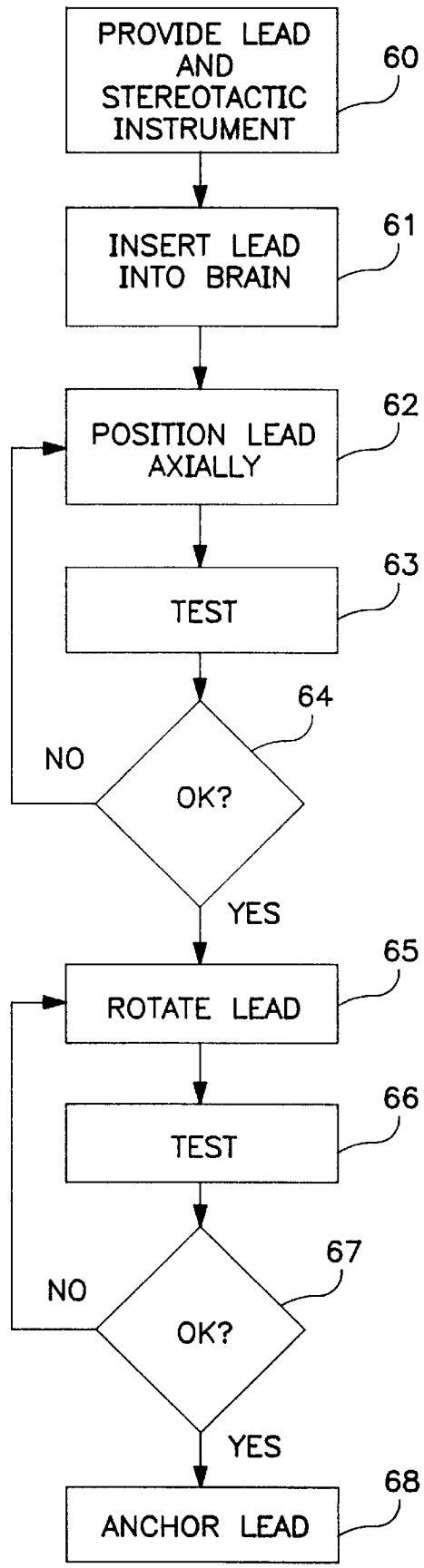
FIG. 4 is a flow diagram illustrating the method of placing the high resolution lead of this invention.

Referring now to FIG. 4, there is shown a simplified flow diagram of the primary steps taken in carrying out the method of implanting and positioning the high resolution lead of this invention. It is assumed that the patient has been prepared in a standard fashion, e.g., a burr hole has been drilled and an anchoring system is ready. At 60, the novel lead of this invention, and the appropriate stereotactic instrument are provided. At 61, the lead is inserted into the brain using the stereotactic instrument and the stylet. At 62, the lead is positioned axially, and tested at 63. If the axial placement is not satisfactory as determined at 64, steps 62 and 63 are repeated. When the distal portion of the lead is positioned at the desired depth with respect to the target in the brain, the lead is then rotated at 65, and the stimulation effectiveness is tested at 66. Rotation will provide, due to the diagonal geometry of the ring segment electrodes, a different stimulation profile, and fine tuning is thus provided which could not be obtained with conventional positioning of the lead. If the position is tested at 67 to not be OK, further rotation and testing is performed until the position is determined to be OK. Such testing can include trying different combinations of electrodes to find an optimum stimulation pattern. After this, the lead is anchored securely at 68, in a known manner.

There has thus been set forth an improved brain stimulation lead and method of placement, which provides a high spatial resolution as is required to optimally stimulate high density brain targets. Although a preferred and alternate embodiments have been set forth specifically, it is to be noted that other variations and equivalent embodiments which use the diagonal geometry of this invention are within the scope of the invention as claimed.

We claim:

1. A stimulation lead for delivery of electrical stimuli to a patient's brain, said lead having a proximal end and a distal end portion of limited length, said distal end portion being substantially cylindrical along a longitudinal axis and having a biocompatible outer coating, a plurality of electrical conductors extending from said proximal end to said distal end portion, and a plurality of electrodes positioned within said distal end portion, each said electrode being connected to a respective one of said conductors, each of said electrodes being a conductive ring which is diagonally positioned with respect to said longitudinal axis on said distal end portion.

2. The lead as described in claim 1, wherein each of said conductive ring electrodes is diagonally positioned at a common angle with respect to said axis, said angle being 45°±15°.

3. The lead as described in claim 2, further comprising a tip electrode at a distal tip end of said distal end portion, said tip electrode being connected to one of said conductors.

4. The lead as described in claim 3, wherein said plurality of conductors comprises 4 conductors, and said plurality of electrodes comprises 3 ring electrodes.

5. The lead as described in claim 3, wherein said distal end portion has a length of no more than about 5 mm.

6. The lead as described in claim 3, wherein there is a separation of about 0.5 to 1.5 mm between each of said electrodes.

7. The lead as described in claim 3, wherein said tip electrode has a diagonal proximal edge at said common angle.

8. The lead as described in claim 3, wherein each of said ring electrodes has a longitudinal width of no more than 0.5 mm.

9. The lead as described in claim 3, wherein said biocompatible coating is polyurethane, and said electrodes are embedded in said polyurethane.

10. The lead as described in claim 3, wherein said distal end portion has an outer diameter no greater than 0.5 mm.

11. The lead as described in claim 1, wherein said ring electrodes extend around said distal end portion an angular distance in a range of 135°–180°.

12. The lead as described in claim 1, wherein said distal end portion is injection molded.

13. The lead as described in claim 3, wherein said tip electrode is spherically configured at its distal end, and diagonally configured at its proximal end.

14. The lead as described in claim 1, wherein each said ring electrode extends around said axis by an angle within the range of 135°–225°.

15. A stimulation lead for delivery of electrical stimuli to a patient's brain, said lead having a proximal end and a distal end portion, said distal end portion being no greater than about 5 mm, said distal end portion having a plurality of conductive ring electrodes positioned at a substantially common diagonal angle with respect to the longitudinal axis of said lead, and a plurality of electrical conductors connecting from respective ones of said electrodes to said lead proximal end.

16. The lead as described as claim 15, wherein each of said ring electrodes extends around said lead by an angle which is less than 180°.

17. The lead as described as claim 15, wherein each of said ring electrodes extends around said lead by an angle which is at least 180°.

18. A method of positioning a stimulation lead in a patient's brain, said lead having a distal end portion carrying a plurality of respective diagonally aligned ring electrodes, comprising:

inserting said lead distal end portion into the patient's brain, positioning said lead axially, rotating said lead and testing stimulation through at least some of said ring electrodes, and anchoring said lead when said stimulation testing is satisfactory.

19. The method as described in claim 18, comprising selecting a combination of said ring electrodes, and connecting said selected combination to a pulse stimulator for stimulating the patient's brain.

* * * * *